United States Patent
Kaiser et al.

(10) Patent No.: US 7,283,870 B2
(45) Date of Patent: Oct. 16, 2007

(54) APPARATUS AND METHOD FOR OBTAINING CARDIAC DATA

(75) Inventors: Willi Kaiser, Emmendingen (DE); Martin Fideis, Freiburg (DE)

(73) Assignee: The General Electric Company, Schenactady, NY (US)

( * ) Notice: Subject to any disclaimer, the term of this patent is extended or adjusted under 35 U.S.C. 154(b) by 194 days.

(21) Appl. No.: 11/186,738

(22) Filed: Jul. 21, 2005

(65) Prior Publication Data

US 2007/0021815 A1  Jan. 25, 2007

(51) Int. Cl.
A61B 5/05 (2006.01)
A61B 5/04 (2006.01)

(52) U.S. Cl. .................. 600/547; 600/509; 607/144

(58) Field of Classification Search .......... 600/509, 600/547, 549; 607/5, 9, 144
See application file for complete search history.

(56) References Cited

U.S. PATENT DOCUMENTS

| | | | | |
|---|---|---|---|---|
| 5,337,753 A * | 8/1994 | Lekhtman | .............. | 600/519 |
| 5,415,176 A * | 5/1995 | Sato et al. | .............. | 600/547 |
| 5,611,351 A * | 3/1997 | Sato et al. | .............. | 600/547 |
| 5,620,003 A * | 4/1997 | Sepponen | .............. | 600/527 |
| 6,370,425 B1 * | 4/2002 | Oguma | .............. | 600/547 |
| 6,398,740 B1 * | 6/2002 | Lavery et al. | .............. | 600/549 |
| 6,402,691 B1 * | 6/2002 | Peddicord et al. | .......... | 600/300 |
| 6,472,888 B2 * | 10/2002 | Oguma et al. | .............. | 324/691 |
| RE37,954 E * | 1/2003 | Sato et al. | .............. | 600/547 |
| 6,519,490 B1 | 2/2003 | Wiesel | | |
| 6,552,553 B2 * | 4/2003 | Shoji et al. | .............. | 324/692 |
| 2002/0151803 A1 * | 10/2002 | Kouou | .............. | 600/483 |
| 2003/0083589 A1 * | 5/2003 | Oguma | .............. | 600/547 |
| 2003/0216654 A1 * | 11/2003 | Xu et al. | .............. | 600/509 |
| 2004/0111120 A1 * | 6/2004 | Sarkar et al. | .............. | 607/5 |
| 2005/0004483 A1 * | 1/2005 | Lin | .............. | 600/509 |
| 2005/0054944 A1 * | 3/2005 | Nakada et al. | .............. | 600/547 |
| 2005/0113703 A1 * | 5/2005 | Farringdon et al. | ......... | 600/509 |
| 2006/0064037 A1 * | 3/2006 | Shalon et al. | .............. | 600/586 |
| 2006/0116589 A1 * | 6/2006 | Park | .............. | 600/500 |
| 2007/0010721 A1 * | 1/2007 | Chen et al. | .............. | 600/300 |
| 2007/0055151 A1 * | 3/2007 | Shertukde et al. | .......... | 600/437 |

FOREIGN PATENT DOCUMENTS

EP   1 147 740   10/2001

OTHER PUBLICATIONS

Webster, ed. *Medical Instrumentation Application and Design 3rd ed.*, New York: Wiley, 1998, pp. 265.

(Continued)

*Primary Examiner*—Angela D. Sykes
*Assistant Examiner*—Christopher A. Flory
(74) *Attorney, Agent, or Firm*—Andrus, Sceales, Starke & Sawall, LLP (57) ABSTRACT

An apparatus and method for obtaining information, such as heart rate or the presence of atrial fibrillation, from electrodes applied to the feet of a subject. A scale having electrodes may be used for this purpose. The signal obtained from the electrodes is digitized and filtered to obtain an electrocardiographic signal exhibiting periodic, sequential, discrete, magnitudinal variations associated with the heartbeats of the subject. The electrocardiographic signal is then analyzed to identify discrete magnitudinal variations useful for obtaining the desired information. In determining the heart rate of the subject, an interval between variations having a desired magnitudinal characteristic may be employed. The absence of such variations is indicative of atrial fibrillation.

20 Claims, 8 Drawing Sheets

OTHER PUBLICATIONS

*Prognostic Significance of a Standard 12-lead ECG after Myocardial Infarction*, W. Zareba, International Journal of Bioelectromagnetism, vol. 5, No. 1, 2003, pp. 289-292.

*Differentialdiagnostik des EKG*, Priv.-Doz. Dr. G. Trieb, et al., 1977, 1981, 1987 F. K. Schattauer Vertagsgesellschaft mbH, ISBN 3-7945-1148-4.

EP Communication/Search Report dated Oct. 20, 2006.

* cited by examiner

APPARATUS AND METHOD FOR OBTAINING CARDIAC DATA

BACKGROUND AND SUMMARY

The present invention relates to an apparatus and method for obtaining cardiac data using conductive elements applied to the feet of a subject. While the invention is not so limited, the invention may be carried out using a body fat analysis scale.

Scales are conventionally used to measure body weight. For a commonly used type of scale, a person steps on footpads on the scale and the resulting compressive loading operates a mechanical or electrical apparatus to provide an indication of the person's weight.

Scales have been developed that can also be used to measure a person's body fat. The footpads on such a scale are made electrically conductive. A small electrical current is passed through the body of a person standing on the footpads. Fat tissue has different electrical properties than muscle tissue, due to differing amounts of water in the different tissues. The bioelectrical impedance that exists between the footpads is measured and used to determine body fat properties, typically the body fat percentage.

BRIEF DESCRIPTION OF THE INVENTION

In an aspect of the invention, information about the heart, such as heart rate or the detection of arrhythmias, may be obtained from the feet of a person, as by using conductive footpads of a scale of the above type.

The heart rate of a person is an important physiological measurement. Increases in the heart rate are indicative of a variety of different diseases and conditions in the body, such as the presence of fever or the consumption of alcohol, caffeine, nicotine, or certain drugs. A permanently high heart rate is a risk predicator for overall mortality as noted in literature such as Wojciech Zaeba, *Prognostic Significance of a Standard 12-Lead ECG after Myocardial Infarction*, International Journal of Bioelectromagnetism, Vol. 5, No. 1, 2003. Hence, it may be desirable to frequently measure a person's heart rate. The convenience of obtaining a person's heart rate by simply stepping on a body fat analysis scale facilitates obtaining such information.

Arrhythmias can occur when the muscle fibers of the heart fail to contract synchronously. This has the potential to lessen the efficiency of the heart to pump blood. In fibrillation, the muscles of the heart quiver randomly and erratically. Ventricular fibrillation is fatal in the absence of immediate medical intervention. However, if the atrial portion of the heart is in fibrillation, the heart can still pump some blood so that the condition can exist until diagnosed and treated.

The detection of atrial fibrillation is important because of its serious nature, because of its frequent existence among the elderly, and because of the adverse prognosis attendant the presence of atrial fibrillation. See Nusser, Trieb, Weidner, *Differentialdiagnostik des EKG*, Schattauer Verlag. In some subjects atrial fibrillation is intermittent in that it is sometimes present and disappears at other times.

A way to check for the existence of atrial fibrillation that is convenient and lends itself to frequent use thus presents further significant health benefits.

To the foregoing ends, electrocardiographic (ECG) signal data is obtained from conductive footpads and processed to identify features, such as the reoccurring QRS complexes appearing in the electrocardiographic data. The timing between successive features is used to determine heart rate. Variations in the timing characteristics among successive heartbeats, or the absence of a heartbeat feature, are indicative of arrhythmias, such as those characterizing atrial fibrillation.

DETAILED DESCRIPTION

Figure 1:
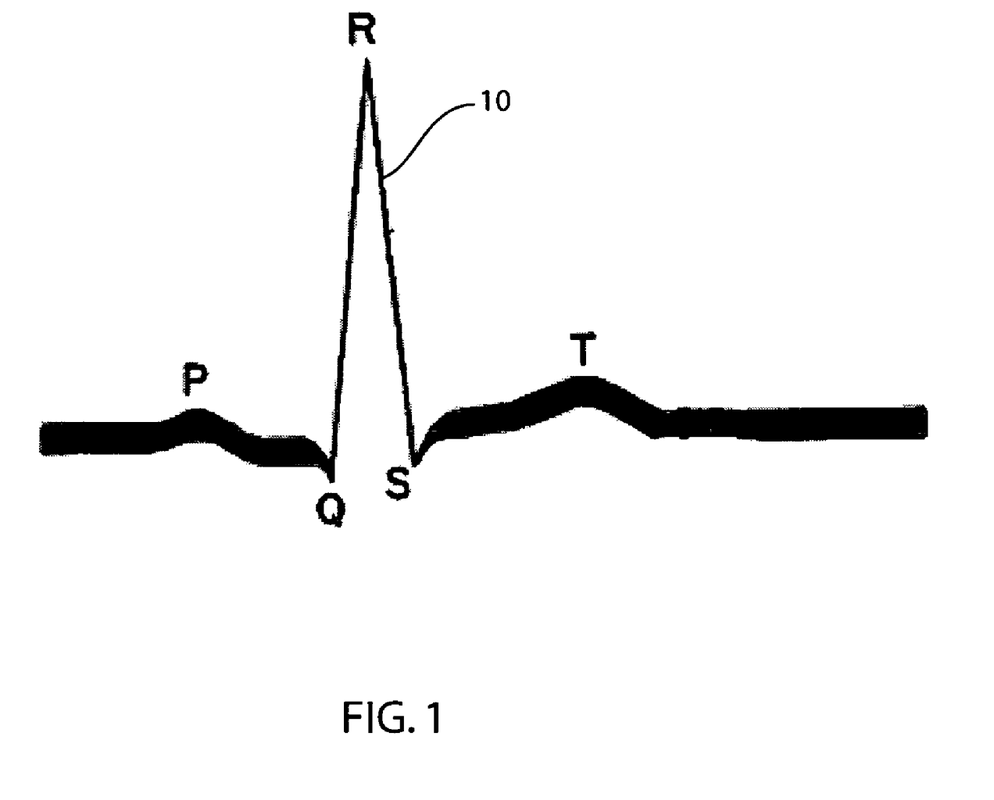
FIG. 1 shows an electrocardiographic signal associated with a heartbeat.

FIG. 1 shows the electrical phenomena or signal 10 associated with a heartbeat, along with the conventional designations for its various components. An initial feature in the morphology of the signal is the P wave resulting from the contraction of the atria of the heart to commence the heartbeat. The major feature of the graph, the QRS complex, is followed by the contraction of the ventricles, and in turn, by the T wave indicative of a refractory period for the heart muscle at the end of the heartbeat. An electrocardiographic signal 10 of the type shown in FIG. 1 is ordinarily obtained by electrodes applied to the chest and extremities of a person.

Figure 2:
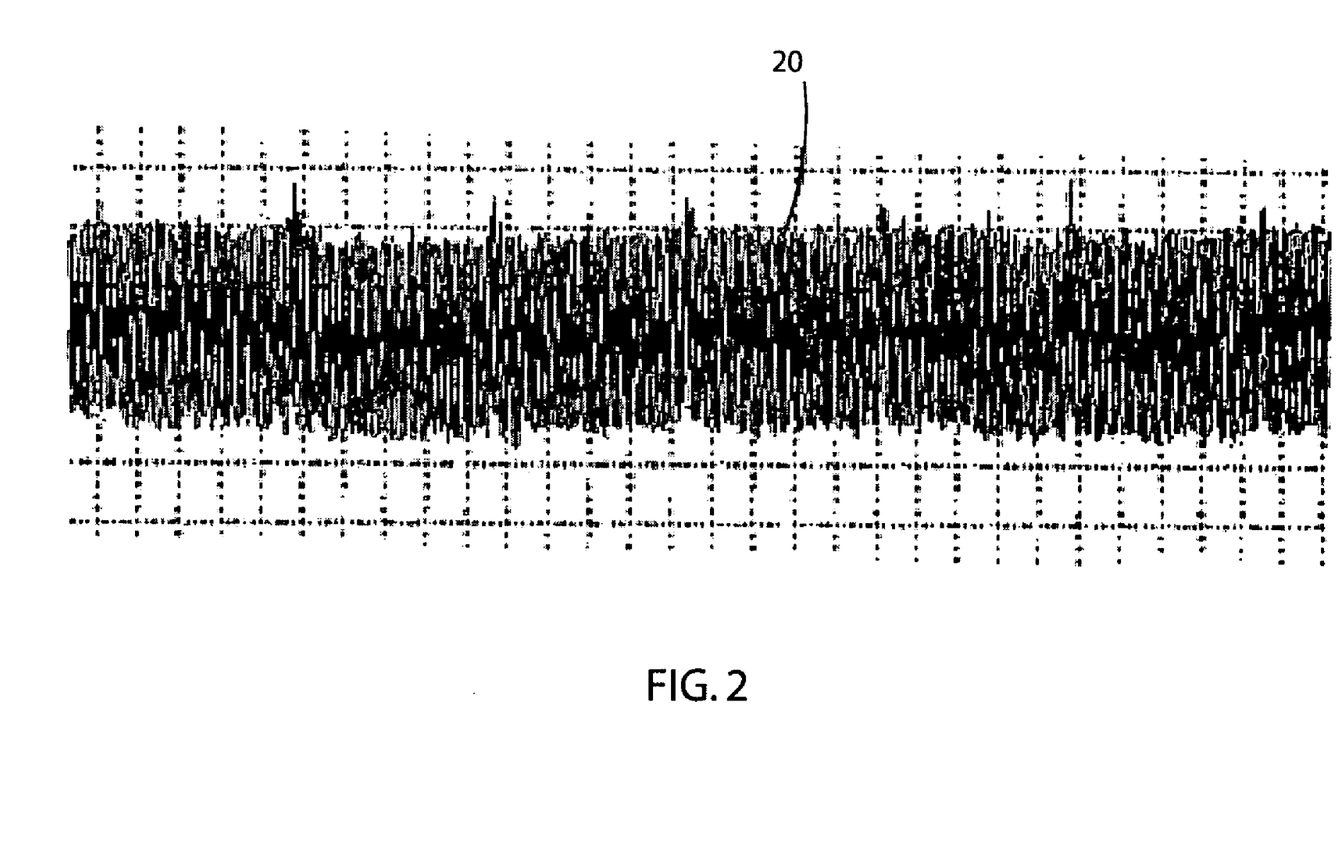
FIG. 2 shows a typical electrical signal obtained from conductive element applied to the feet of a person.

FIG. 2 shows a typical electrocardiographic signal 20 received from the feet of a person containing a small magnitude ECG signal and a considerable amount of electrical noise in the output from conductive footpads applied to the feet.

Figure 3:
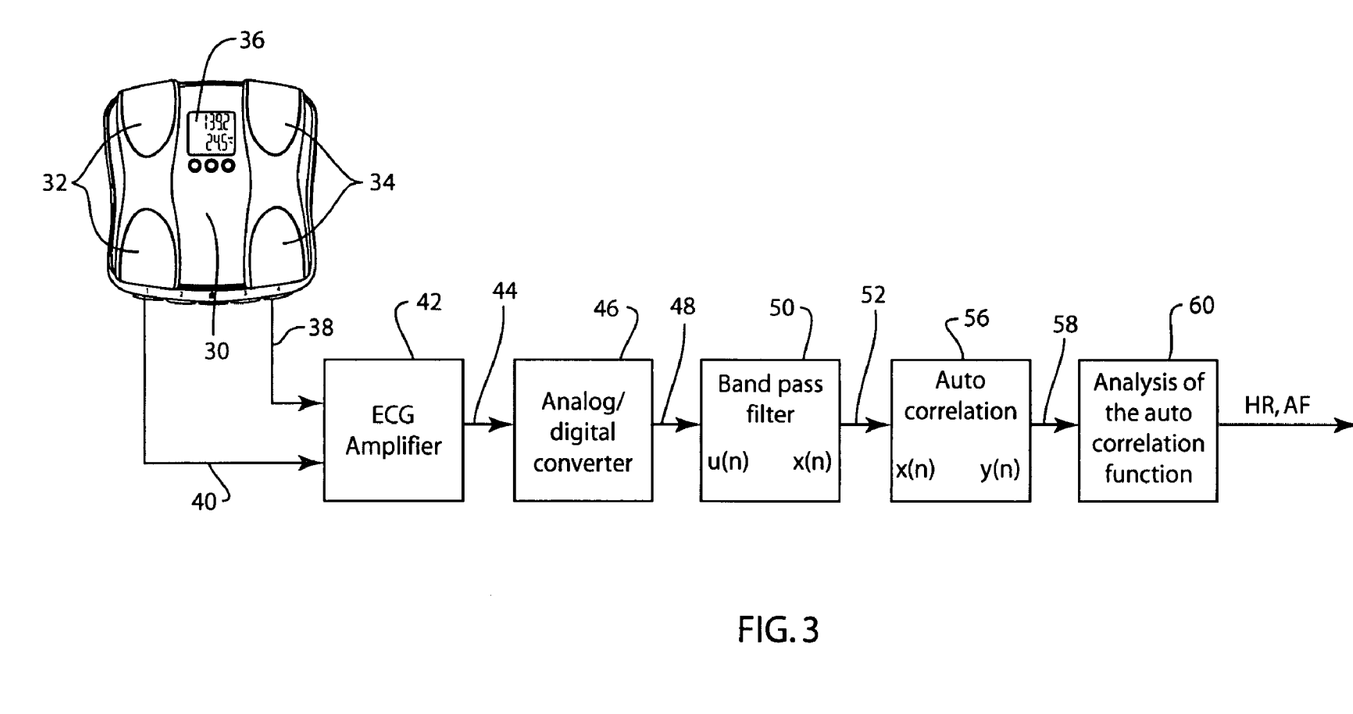
FIG. 3 shows an embodiment of the present invention suitable for obtaining cardiac data from an electrical signal of the type shown in FIG. 2.

FIG. 3 shows apparatus for obtaining information about the heart from output signal 20 obtained from electrodes applied to the feet of a person. Scale 30 has pairs of conductive footpads 32 and 34 on which a subject stands to determine his/her body weight and body fat. While the invention is not so limited, the use of pairs of footpads increases the quality of data collected as one set of footpads may be used for data collection and the other set used for common mode rejection of noise. Scale 30 has display 36 for providing this information. Leads 38 and 40 extend from scale 30 to provide the output signal shown in FIG. 2.

Leads 38 and 40 are connected to input ECG amplifier 42 having appropriate characteristics of frequency response, gain, circuit protection, and the like. The ECG lead signal output from amplifier 42 is provided in conductor 44 to analog/digital converter 46. Analog/digital converter 46 samples the signal in conductor 44 at an appropriate rate and converts the analog signal in conductor 44 to a digital signal in conductor 48. The minimum sampling rate to collect data that will reproduce a signal accurately is two times the highest frequency component of the signal, as determined by Nyquist's theorem. Therefore a sampling rate of at least twice the line frequency is required to filter out the line frequency. In an embodiment of the invention, a sampling rate of 200 Hz is used when the line frequency is 50 Hz or 240 Hz is used when the line frequency is 60 Hz.

The signal in conductor 48 is supplied to bandpass filter 50 that carries out high pass and low pass filtering of the signal to improve the signal to noise ratio over that found in the digital signal in conductor 48. In an embodiment of the invention, the bandpass filter 50 may have a low frequency cutoff at 2 Hz and a high frequency cutoff at 25 Hz. As a result of bandpassing only a selected portion of the total signal shown in FIG. 2, QRS complexes, P-waves, and T-waves found in the bandpassed signal are augmented and the noise in the signal is reduced. That is, the signal shown in FIG. 2 may contain noise frequency components in a range from 0-1,000 Hz whereas the signal in conductor 52 will contain only noise components between 2-25 Hz so that a substantial amount of the frequency content of the signal is removed by the bandpass filter. This results in leaving the predominant ECG signal while removing a substantial amount of the noise, as can be seen by comparing FIGS. 2 and 4.

The high pass filter found in element 50 may comprise an infinite impulse response (IIR) filter. An IIR filter is suited for use as a high pass filter because a lower order and easier to calculate and implement filter of this type will provide a steeper cut-off frequency. An IIR filter also provides faster real-time signal processing also making it advantageous for use as a high-pass filter. The low pass filter found in element 50 may comprise a finite impulse response (FIR) filter. A FIR filter is appropriate for a low pass filter due to its stability and linear phase response and the ability to reject 60 Hz or 50 Hz line noise. It will be appreciated that other types of filters and sampling rates may be used in the apparatus shown in FIG. 3.

Figure 4:
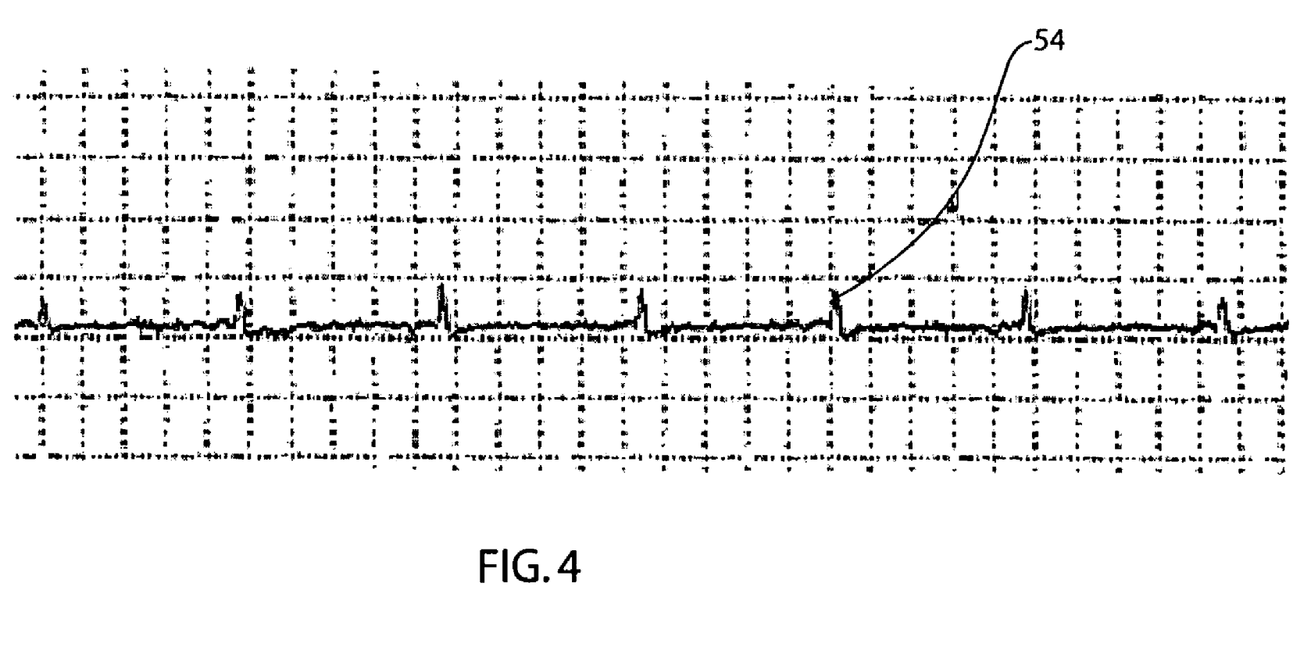
FIG. 4 shows an electrocardiographic signal provided at the output of a bandpass filter element of the apparatus of FIG. 3.

The output from bandpass filter 50 in conductor 52 is shown in FIG. 4 as the graph 54. It will be appreciated from an inspection of FIG. 4 that the features of the electrocardiographic data shown in FIG. 1 are augmented in the signal 54 in conductor 52 in the process of filtering signal 20 shown in FIG. 2. This includes the prominent QRS complex of the electrocardiographic signal shown in FIG. 1.

The signal 54 in conductor 52 is supplied to element 56 that performs an autocorrelation on the signal. An autocorrelation is carried out by comparing and correlating a signal with itself. An autocorrelation function measures the dependence of time series values at one time on the values of that time series at another time. A modified autocorrelation is calculated by equation (1):

$$y(k) = \frac{\sum_{n=1}^{N-K} x(n)x(n+k)}{\sum_{n=1}^{N-K} x(n)^2} \qquad (1)$$

Given the time series x(n), x(n+k), n=1, 2 ... N, k=1, 2 ... K

By definition, over a large time series, a stochastic or random process tends towards being a zero-mean time series, thus having an autocorrelation of zero. Therefore, the autocorrelation removes any random signal processes, leaving the desired underlying periodic signal, in this case the ECG signal. An autocorrelation function is most useful in extracting an underlying periodic signal out of random background noise including circumstances in which the underlying signal is masked by high amplitude and high frequency noise. This is the case in ECG signal processing. In element 56, the autocorrelation function pulls the ECG signal out of the underlying noise in the signal 54 in conductor 52 and provides the same to analysis element 60 in conductor 58.

The analysis of the autocorrelation function is carried out in the following manner as shown graphically in FIG. 5. The signal in conductor 58 is examined to locate a maximum spike amplitude 62 found in the autocorrelation function y(k). A threshold value is then defined as a percentage of the maximum spike amplitude. For example, the threshold may be set at 60% of the spike amplitude. This permits information about the heart to be determined even in the presence of ventricular and supraventricular extrasystoles. Extrasystoles, or premature beats, are typically contractions of the ventricles that do not alter the fundamental rhythm of the heart or inject significant amounts of blood into the circulatory system.

Thereafter, the distance or timing from a first spike to a second spike that exceeds the threshold is determined. This is shown as the quantity K in FIG. 5.

When K is considered as a time quantity, such as 0.8 seconds between spikes, the formula for determining heart rate in beats per minute is $$HR=60/K \qquad (2)$$

Due to the sampling carried out in analog/digital converter 46, it is often more convenient to express K as the number of samples between spikes. In this case, the formula would be $$HR=(60 \times \text{sampling rate})/K \qquad (3)$$

The heart rate of a person standing on scale 30 is thus determined from the feet of the person. Typically 10 seconds of data may be used to determine the heart rate. The heart rate so determined may be provided to display 36 of scale 30.

Figure 6:
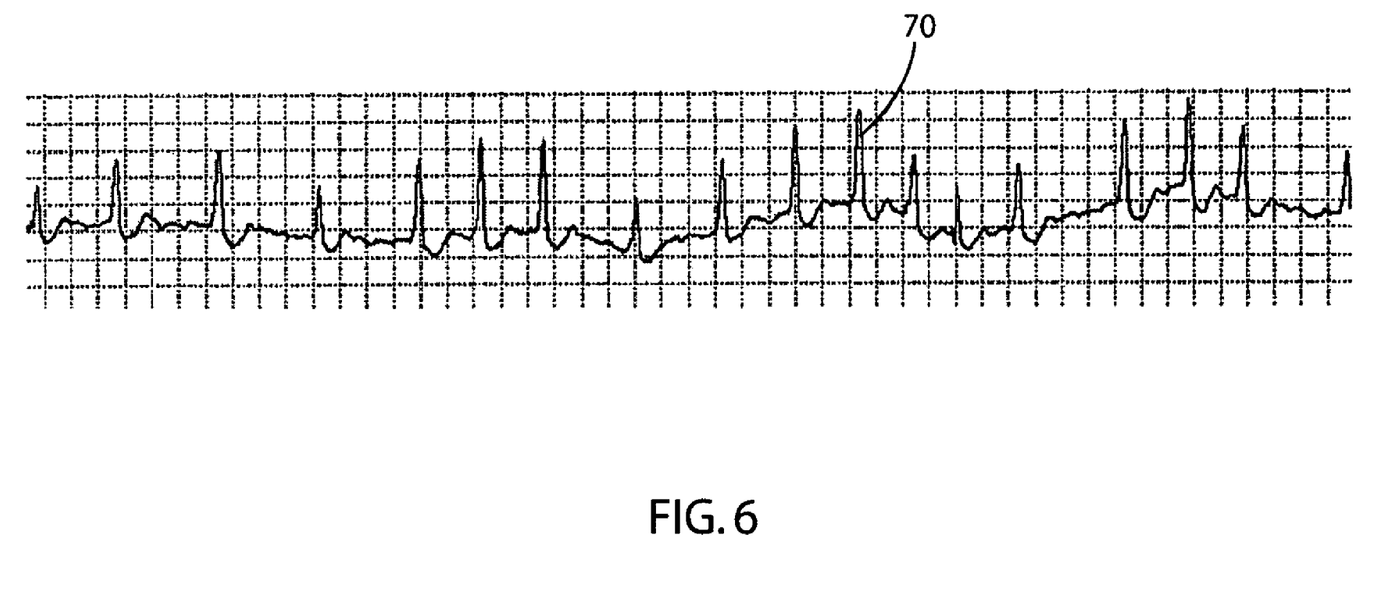
FIG. 6 shows an electrocardiographic signal exhibiting high variability in the heartbeats and indicative of the presence of atrial fibrillation.

FIG. 6 shows an electrocardiographic signal 70 for a subject who is experiencing atrial fibrillation, as indicated by the high variability in the intervals between the QRS complexes in the ECG signal and the poor definition, or lack, of characteristics, such as the P wave.

Figure 5:
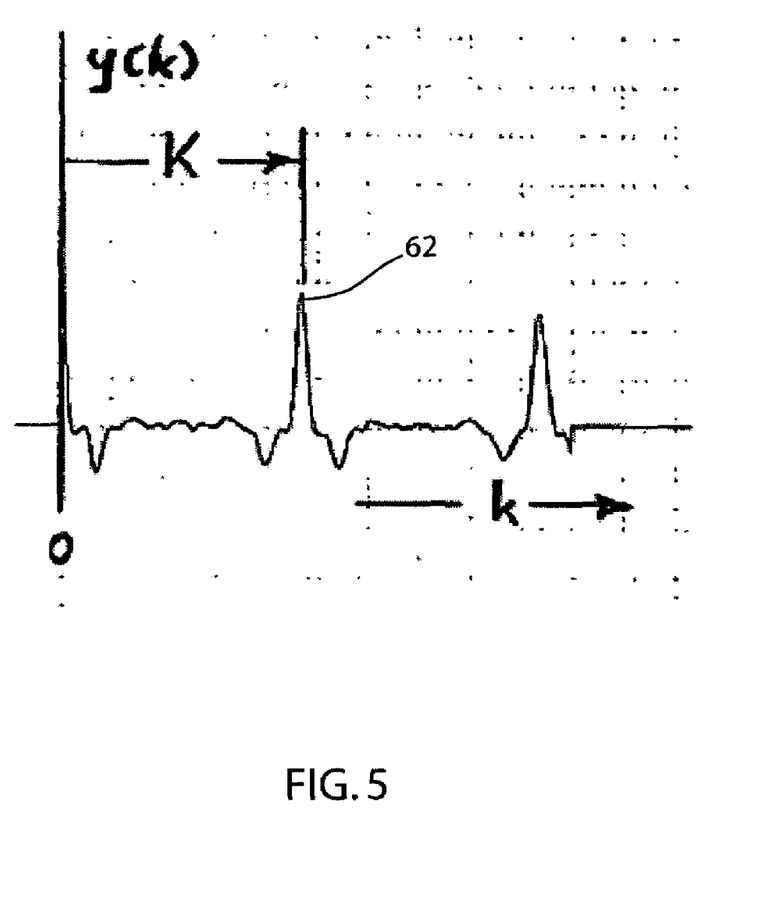
FIG. 5 shows an autocorrelation function of the electrocardiographic signal of FIG. 4 and the manner in which the function is used to obtain cardiac data such as a person's heart rate.
Figure 7:
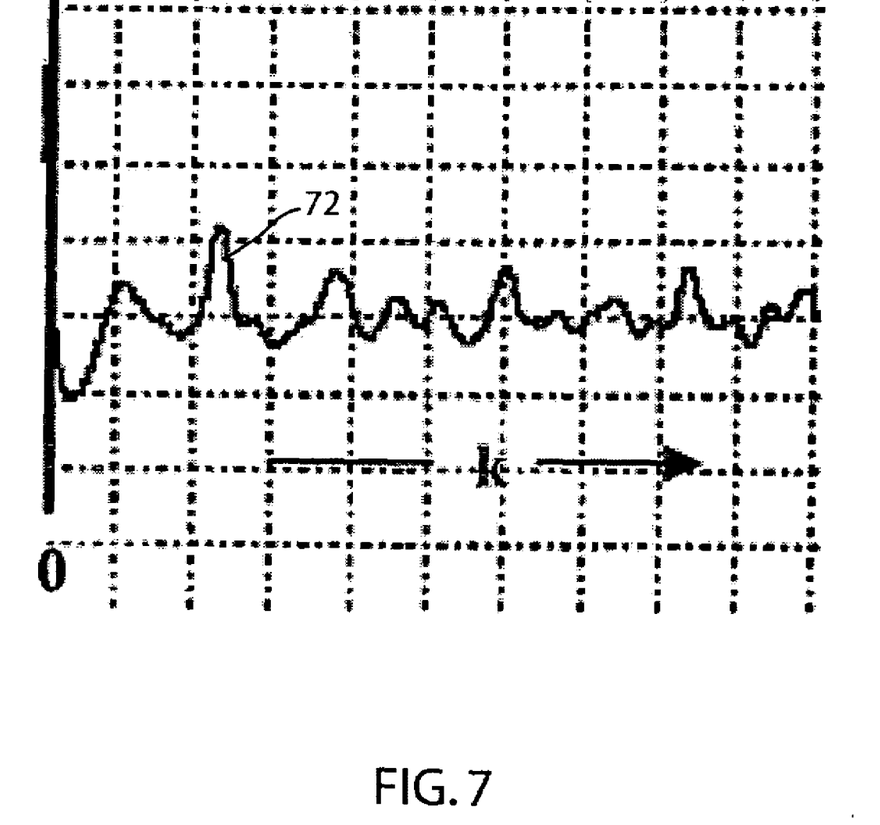
FIG. 7 shows the autocorrelation function of the signal of FIG. 6.

FIG. 7 shows the autocorrelation function for the signal 70 of FIG. 6 in a manner corresponding to that of FIG. 5 showing a normal ECG signal. As can be seen from FIG. 7, the high variability, or conversely the low regularity, in the periodicity of the signal 70 shown in FIG. 6 results in low magnitude spikes in the autocorrelation function 72 of FIG. 7. As a result, none of the spikes will exceed the threshold established in analysis element 60 and this phenomenon may be used to provide an indication at output of element 60 that the subject from whom the data is obtained is experiencing atrial fibrillation.

While discrete components are shown for illustrative purposes in FIG. 3 and to facilitate an explanation of the disclosed apparatus, it will be appreciated that many of the components may be formed by an appropriately programmed microprocessor or central processing unit (CPU), including that found in scale 30 for use in determining body weight and fat.

Figure 8:
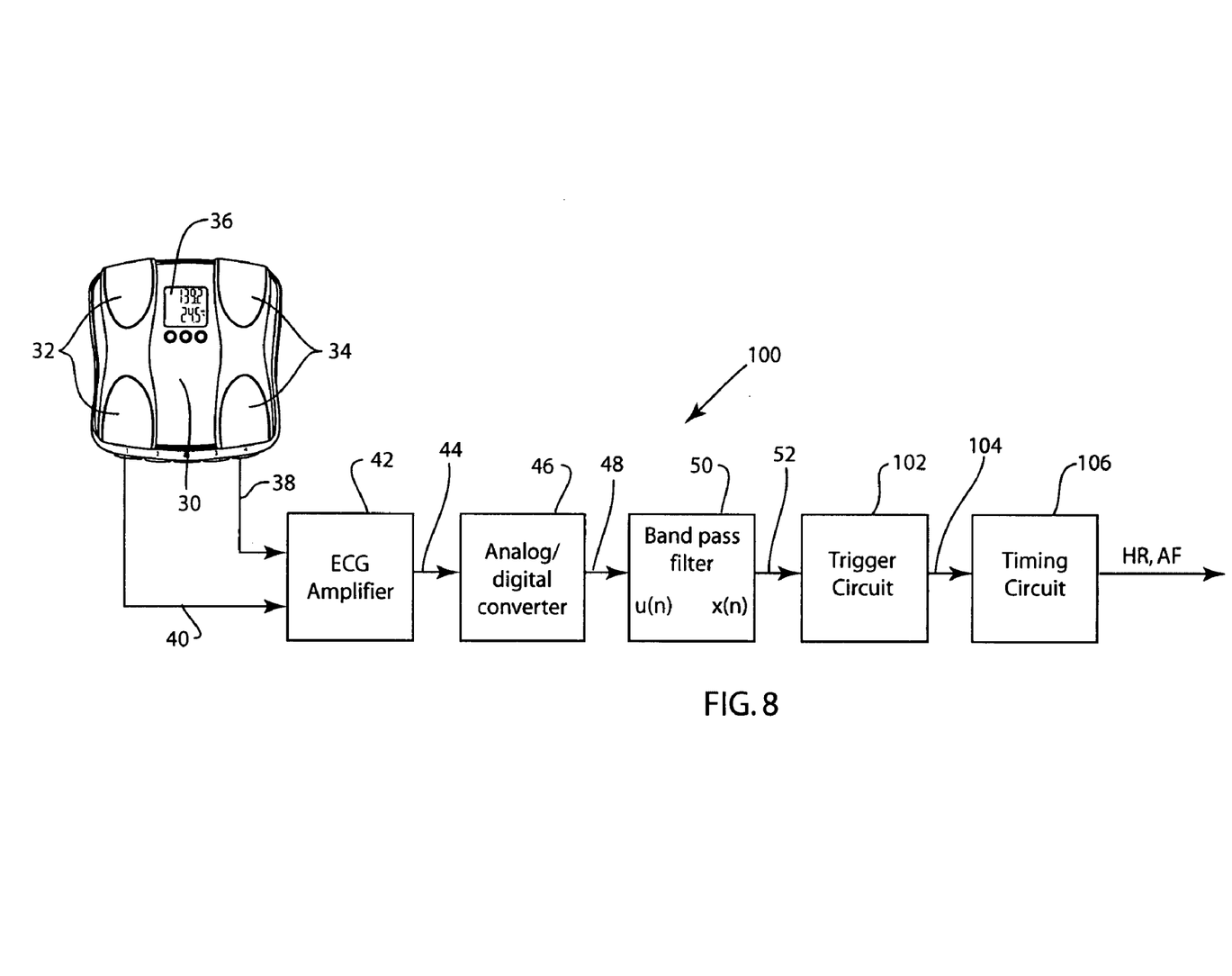
FIG. 8 shows a further embodiment of the apparatus of the present invention.

FIG. 8 shows another embodiment of apparatus suitable for carrying out the present invention. Apparatus 100 shown in FIG. 8 employs QRS trigger element 102. QRS trigger element 102 employs the magnitude or rate of change properties contained in the filtered signal 54 in conductor 52 to identify the QRS complexes in signal 54. For example, a digital equivalent of a Schmitt trigger may be used for this purpose. In such a circuit, a change in state of the output signal is "triggered" when the input signal crosses a predetermined threshold level. The output of QRS trigger element 102 is provided in conductor 104 to element 106 that includes timing or other circuitry to identify the interval between successive QRS complexes. For example, the interval between the feature in signal 54 corresponding to the R feature of the QRS complex in the ECG signal may be determined. The average of the duration of a series of intervals between R features, the average PR interval, for example from 10 seconds of ECG signal data is inserted in equation (4) to obtain the heart rate.

$$HR = 60/\text{average } RR \text{ interval} \quad (4)$$

For the detection of atrial fibrillation, the irregularity in the intervals between QRS complexes may be used for this purpose. Or, an average or median heart beat characteristic comprising the PQRST-data for a given number of cycles, for example 10 cycles, may be determined from the signal in conductor 104. As noted above in atrial fibrillation, the P-wave is absent or ill-defined. The absence of at least a proper P-wave within the time of an average or median heart beat may be used to detect atrial fibrillation.

It will be appreciated that the present invention provides a convenient, simple way for a person to learn of an important health criteria from a small and noisy signal obtained from the feet. The information so obtained can be used along, or in connection, with other information, such as weight and body fat determined from a scale.

Various alternatives and other embodiments are contemplated as being within the scope of the present invention. For example, it is possible to provide the ability to enter age and gender information into the apparatus to personalize the data analysis carried out by analysis element 60 thus increasing the usefulness of the obtained cardiac data, for example, the accuracy of atrial fibrillation determination. Or, by using data storage capabilities, the analysis carried out by element 60 can be modified based on past data or over time, thus increasing the accuracy of data analysis. Data storage capability also allows for long-term analysis and trending of the collected physiological parameters. The data obtained by the apparatus may be communicated via RF, modem, or broadband technology to a related data collection site, such as a healthcare provider. Alternatively, the communication ability may comprise RF, infrared or serial connection to a data storage unit, a computer, or a printer.

What is claimed is:

1. A method for obtaining cardiac information from a person, said method comprising the steps of:
    applying electrodes to the feet of the person to obtain a bioelectrical signal from the person including cardiac data;
    filtering the bioelectric signal to provide a filtered signal containing the cardiac data;
    processing the filtered signal to identify discrete magnitudinal variations in the signal useful for obtaining atrial fibrillation information;
    determining a characteristic of the discrete variations; and
    using the determined characteristic to obtain atrial fibrillation information from the person.

2. The method according to claim 1 further defined as determining an interval property between successive discrete variations.

3. The method according to claim 2 further defined as using the determined interval property to obtain the heart rate of the person.

4. The method of claim 2 further defined as using variation in the interval property between discrete magnitudinal variations to obtain information regarding atrial fibrillation in the person.

5. The method according to claim 1 further defined as using the absence of a morphological feature of a heartbeat feature to obtain information regarding atrial fibrillation in the person.

6. The method according to claim 5 wherein properties of an average beat of the heart of a person are determined and the absence of a morphological feature of a heartbeat within the time period of an average beat is indicative of atrial fibrillation.

7. The method according to claim 1 wherein the step of processing the filtered signal is further defined as including the step of calculating an autocorrelation function for the filtered signal and the step of determining a characteristic of the discrete variation is further defined as
    identifying a maximum spike amplitude in the autocorrelation function,
    defining a spike threshold value based on the maximum spike amplitude, and
    analyzing the autocorrelation function to determine the interval from a first spike that exceeds the threshold value to a subsequent second spike that exceeds the threshold value.

8. The method according to claim 1 wherein the filtering step is further defined as bandpass filtering the digitized signal.

9. The method according to claim 1 wherein the identified discrete magnitudinal variation corresponds to a QRS complex in the cardiac data and; wherein the processing of the filtered signal employs a QRS trigger.

10. The method according to claim 1 wherein the step of applying the electrodes is further defined as the act of a person stepping on a scale having electrodes.

11. The method according to claim 1 wherein the step of applying the electrodes is further defined as applying two pairs of electrodes to the feet of the person.

12. Apparatus for obtaining cardiac information from a person, said apparatus comprising:
    electrodes appliable to the feet of the person to obtain a bioelectrical signal from the person containing cardiac data;
    a filter receiving said bioelectrical signal and providing a filtered signal containing the cardiac data;
    a processor configured to process the filtered signal to identify discrete magnitudinal variations in the signal useful for obtaining atrial fibrillation information;
    means for determining a characteristic of the discrete variations; and
    means for using the determined characteristic to obtain atrial fibrillation information from the person.

13. The apparatus according to claim 12 wherein said determining means is further defined as determining an interval property between successive discrete variations.

14. The apparatus according to claim 12 wherein said means for using is further defined as using the determined interval property to obtain the heart rate of the person.

15. The apparatus according to claim 12 wherein said means for using is further defined as using variation in the interval property between discrete magnitudinal variations to obtain information regarding atrial fibrillation in the person.

16. The apparatus according to claim 12 wherein said determining means is further defined as determining the absence of a morphological feature of a heartbeat to obtain information regarding atrial fibrillation in the person.

17. The apparatus according to claim 12 wherein the processor further comprises a means for calculating an autocorrelation function for the filtered signal.

18. The apparatus according to claim 12 wherein the processor further comprises a QRS trigger for identifying discrete magnitudinal variations in the signal.

19. The apparatus according to claim 12 wherein said filter is further defined as a band pass filter.

20. Apparatus for obtaining cardiac information from a person on a scale, said apparatus comprising:

electrodes appliable to the feet of the person to obtain a bioelectrical signal containing cardiac data from a person standing on the scale;

a bandpass filter receiving said bioelectrical signal and providing a bandpassed signal containing the cardiac data;

means for calculating an autocorrelation function of the bandpassed signal to identify discrete magnitudinal variations in the signal useful for obtaining atrial fibrillation information;

means for determining a characteristic of the discrete variations; and means for using the determined characteristic to obtain the atrial fibrillation information from the person.

* * * * *

UNITED STATES PATENT AND TRADEMARK OFFICE
CERTIFICATE OF CORRECTION

| | | |
|---|---|---|
| PATENT NO. | : 7,283,870 B2 | Page 1 of 1 |
| APPLICATION NO. | : 11/186738 | |
| DATED | : October 16, 2007 | |
| INVENTOR(S) | : Willi Kaiser and Martin Findeis | |

It is certified that error appears in the above-identified patent and that said Letters Patent is hereby corrected as shown below:

On Title Page: Item (75)Inventors:

Delete "Martin Fideis" and replace with --Martin Findeis--, Freiburg (DE)

Signed and Sealed this

Twenty-fifth Day of December, 2007

JON W. DUDAS
*Director of the United States Patent and Trademark Office*